United States Patent [19]
Lauren

[11] Patent Number: 5,431,060
[45] Date of Patent: Jul. 11, 1995

[54] DUAL CAPABILITY TENSILE TESTING MACHINE

[76] Inventor: Mark D. Lauren, 239 Anderson Pl., Buffalo, N.Y. 14222

[21] Appl. No.: 78,568

[22] Filed: Jun. 17, 1993

[51] Int. Cl.$^6$ .............................................. G01N 3/08
[52] U.S. Cl. ...................................... 73/831; 73/826; 73/856; 374/49
[58] Field of Search ................ 73/826, 831, 833, 834, 73/796, 856, 860, 837; 374/49, 50

[56] References Cited

U.S. PATENT DOCUMENTS

| | | | |
|---|---|---|---|
| 2,545,482 | 3/1951 | Manjoine et al. | 73/826 |
| 2,689,474 | 9/1954 | Wachtel | 73/16 |
| 3,859,848 | 1/1975 | Dripke | 73/796 |
| 3,994,158 | 11/1976 | Weinhold | 73/825 |
| 4,018,080 | 4/1977 | Fletcher et al. | 73/796 |
| 4,114,420 | 9/1978 | Browning | 73/826 |
| 4,266,424 | 5/1981 | Muenstedt | 73/826 |
| 4,478,086 | 10/1984 | Gram | 73/781 |

FOREIGN PATENT DOCUMENTS 1384759 2/1975 United Kingdom .................. 374/49

OTHER PUBLICATIONS

Cryostat For Tension Testing In The Temperature Range 4° to 300° K. by G. U. Behrsing and L. R. Lucas—Published in The Review Of Scientific Instruments, vol. 36(5): pp. 617–620—May 1965.
Thermodynamics Of Shrinkage Of Fibrous (Racked) Rubber by J. F. M. Oth and P. J. Flory—Published in Journal American Chemical Association—vol. 80: pp. 1297–1304—Mar. 20, 1958.

Primary Examiner—Hezron E. Williams
Assistant Examiner—Nashmiya Ashraf
Attorney, Agent, or Firm—Joseph P. Gastel

[57] ABSTRACT

A convertible tensile test machine having a dual capability for selectively testing a specimen in an open environment or in solution including a frame having an upper portion and a lower portion and a central portion therebetween, a support plate on the central portion of the frame, a carriage on the frame above the support plate on the upper portion of the frame, a load cell transducer on the carriage, a drive for driving the carriage toward and away from the support plate, an upper grip on the load cell transducer, a lower grip on the lower portion of the frame below the support plate, an opening in the support plate, a connector member connected to the upper grip and extending through the opening in the support plate for connection to the upper end of a specimen, the lower end of which is connected to the lower grip for open environment testing, a shelf mountable on the lower portion of the frame for supporting a vessel for solution testing, a second lower grip, a carrying member attachable to the support plate for carrying the second lower grip for immersing the second lower grip in the vessel, and an opening in the carrying member for receiving the connector member for attachment to an upper end of a specimen, the lower end of which is connected to the second grip contained in the vessel.

9 Claims, 4 Drawing Sheets

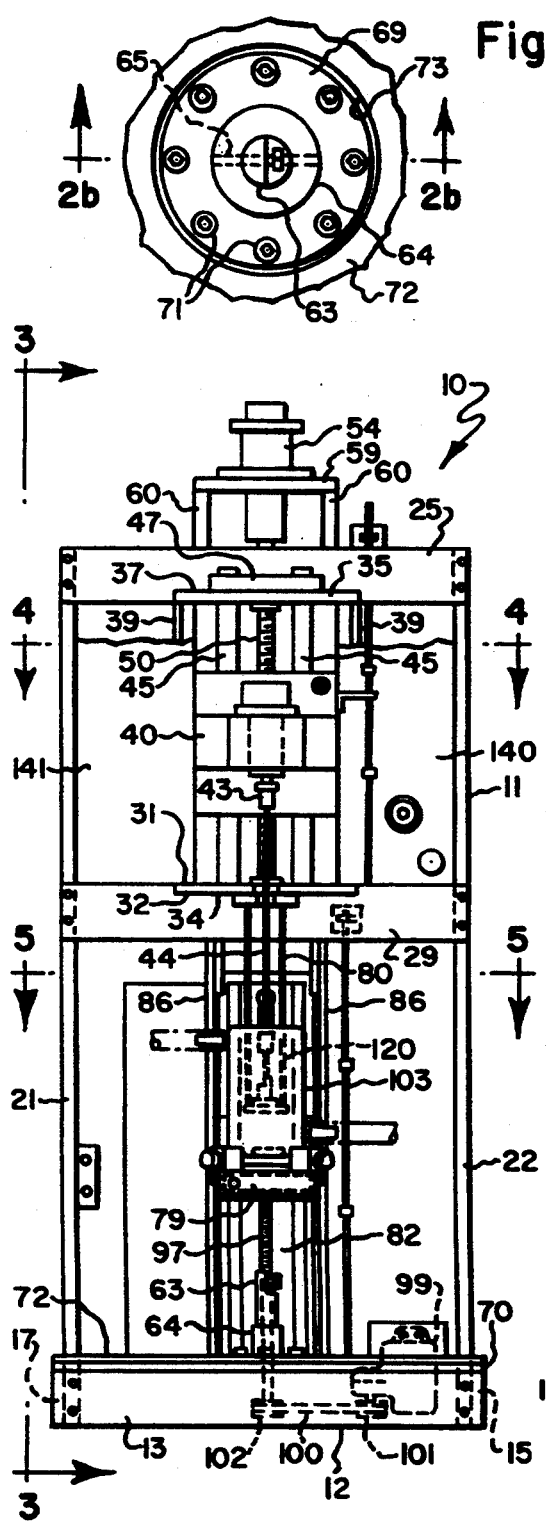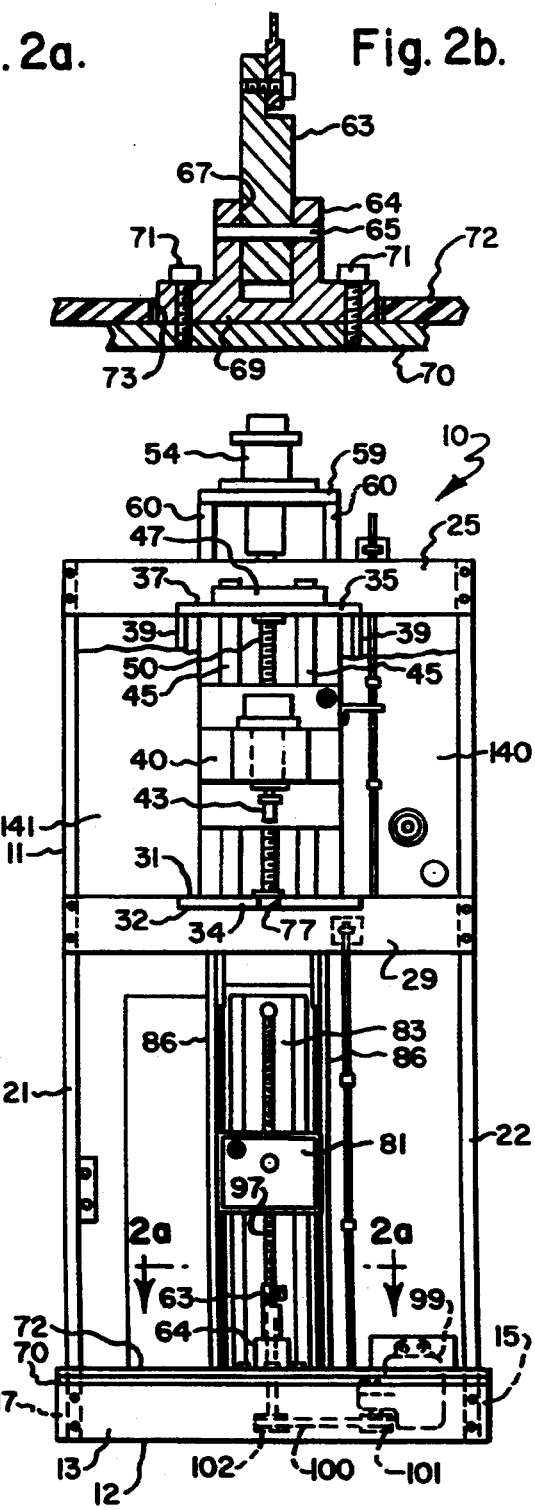

Fig. 6.
Fig. 9.
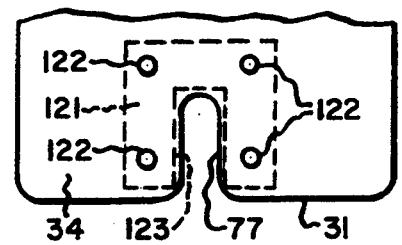
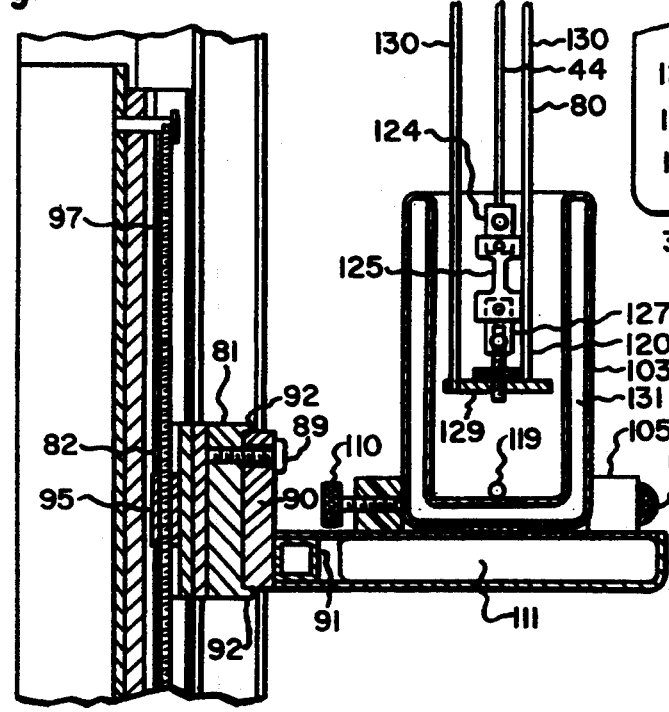
Fig. 7.
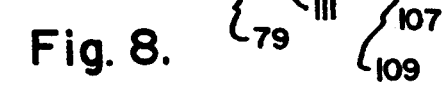
Fig. 8.

DUAL CAPABILITY TENSILE TESTING MACHINE

BACKGROUND OF THE INVENTION

The present invention relates to a dual capability tensile testing machine for testing specimens both in the open environment and in solution.

By way of background, there are in existence tensile testing machines which are designed to test specimens in the open environment, but these same machines are not capable of evaluating mechanical properties of materials in temperature-controlled solutions for maintaining specimens continuously wetted or for allowing chemical reactions to take place thereon. Mechanical testers may be modified to perform tests in solution, but such modifications are generally very expensive because the original design of presently available testers, insofar as known, is not amenable to such modifications. Complete materials characterization often requires comparing the behavior of specimens exposed to specific chemical environments with that exhibited under open environment conditions.

SUMMARY OF THE INVENTION

It is accordingly one object of the present invention to provide a tensile testing machine which is specifically designed to either perform mechanical tensile testing in solution or in an open environment and which can be easily reconfigured to perform either type of testing. Other objects and attendant advantages of the present invention will readily be perceived hereafter.

The present invention relates to a convertible tensile test machine having a dual capability for selectively testing specimens in an open environment or in solution comprising a frame, first means on said frame for selective tensile testing a specimen in the open environment, and second means selectively mountable on said frame for selective tensile testing of a specimen in solution and selectively demountable from said frame to reconfigure said machine for testing in the open environment.

The present invention also relates to a convertible tensile test machine having a dual capability for selectively testing a specimen in the open environment or in solution comprising a frame, an upper grip assembly on said frame carrying an upper grip for gripping the upper portion of a specimen, a lower grip assembly carrying a lower grip aligned with said upper grip on said frame for gripping the lower portion of a specimen during open environment testing, shelf means selectively mountable between said upper and lower grips for supporting a vessel which is to contain solution, and a second lower grip assembly selectively mountable on said frame for carrying a second lower grip for alignment with said upper grip and for attachment to the lower portion of a specimen which is to be immersed in solution in a vessel supported on said shelf.

The various aspects of the present invention will be readily perceived when the following portions of the specification are read in conjunction with the accompanying drawings wherein:

BRIEF DESCRIPTION OF THE DRAWINGS

FIG. 1 is a front elevational view of the dual capability convertible tensile test machine of the present invention configured for testing specimens in solution;

FIG. 2 is a front elevational view of the convertible tensile test machine configured for testing specimens in an open environment;

FIG. 2a is a fragmentary view taken substantially in the direction of arrows 2a—2a of FIG. 2 showing the attachment member or grip for attachment to a specimen which is to be tested in the open environment;

FIG. 2b is a fragmentary cross sectional view taken substantially along line 2b—2b of FIG. 2a;

FIG. 6 is an enlarged fragmentary cross sectional view taken substantially along line 6—6 of FIG. 5;

FIG. 7 is an enlarged exploded view of the shelf and its mounting structure of FIG. 5;

FIG. 8 is a fragmentary enlarged cross sectional view taken substantially along line 8—8 of FIG. 3 and showing various details of the structure utilized in the testing of specimens in solution; and FIG. 9 is a fragmentary plan view taken substantially in the direction of arrows 9—9 of FIG. 8 and showing the relationship between the support plate of the machine and the attachment plate for mounting the specimen attachment structure for use in testing specimens in solution.

DESCRIPTION OF THE PREFERRED EMBODIMENTS

Summarizing briefly in advance, the convertible test machine 10, as noted above, is utilized for selectively testing specimens in an open environment or testing specimens in solution. This dual capability is achieved through the combination of special interchangeable lower assemblies for gripping or attaching specimens for testing in the open environment or through detachable assemblies for testing in solutions, and the machine can be easily reconfigured from one status to the other.

Figure 3:
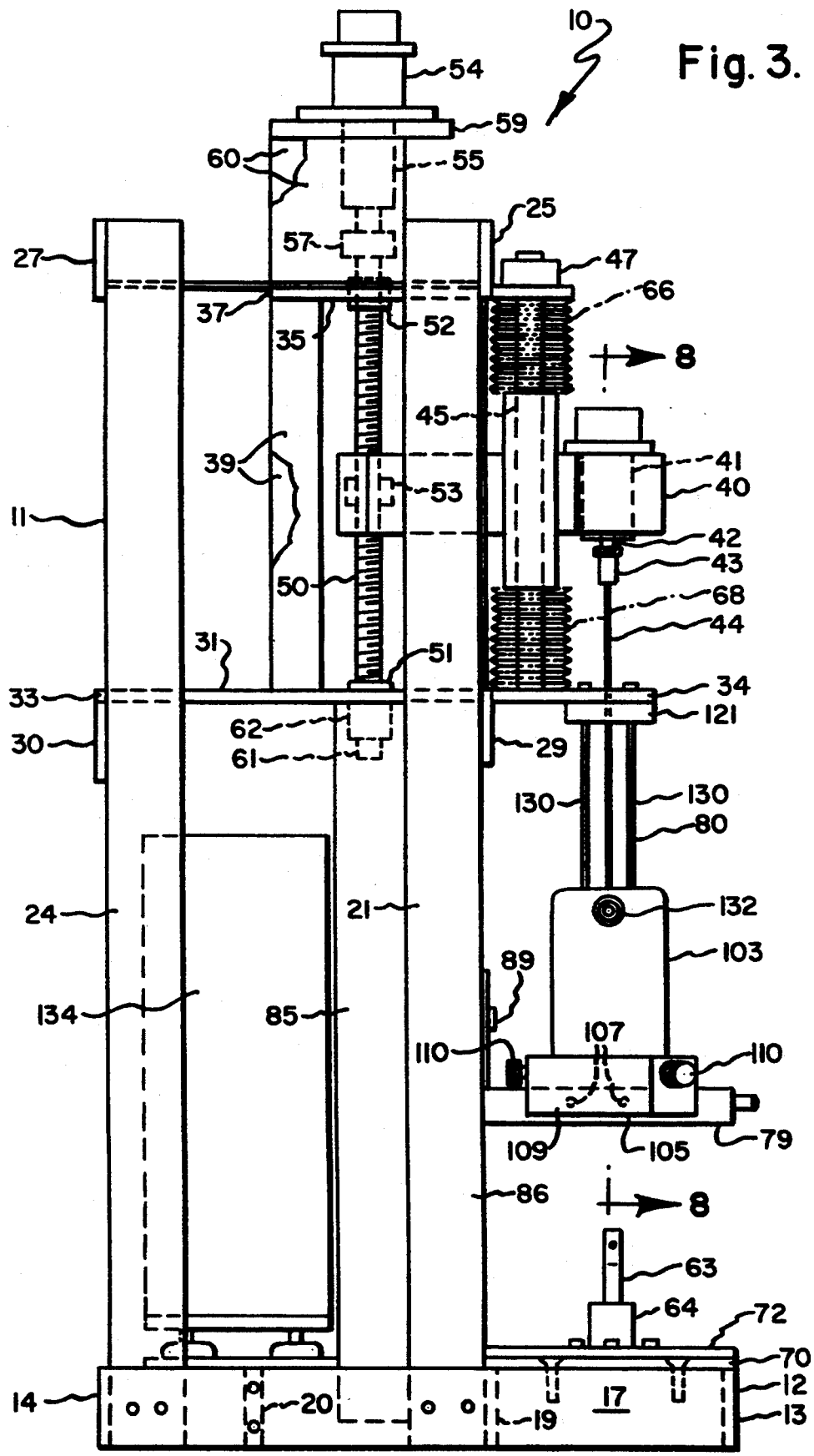
FIG. 3 is an enlarged side elevational view of the embodiment of FIG. 1 taken substantially in the direction of arrows 3—3 of FIG. 1.
Figure 4:
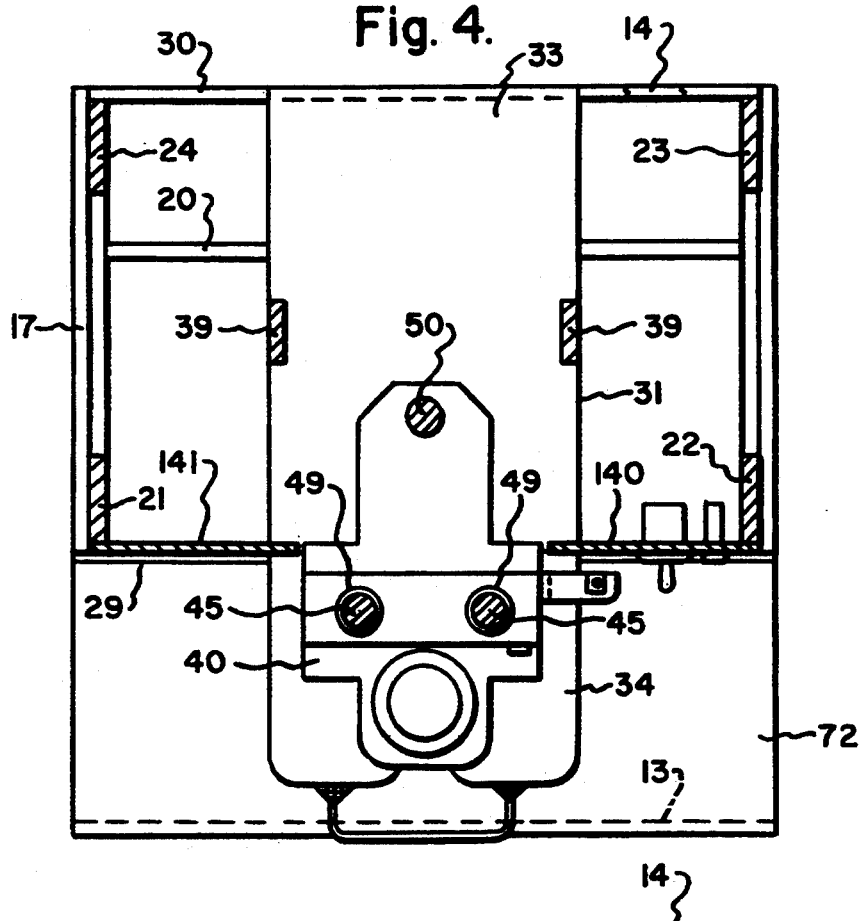
FIG. 4 is a cross sectional view taken substantially along line 4—4 of FIG. 1 and showing various details of the load cell carriage and the mounting structure therefor.
Figure 5:
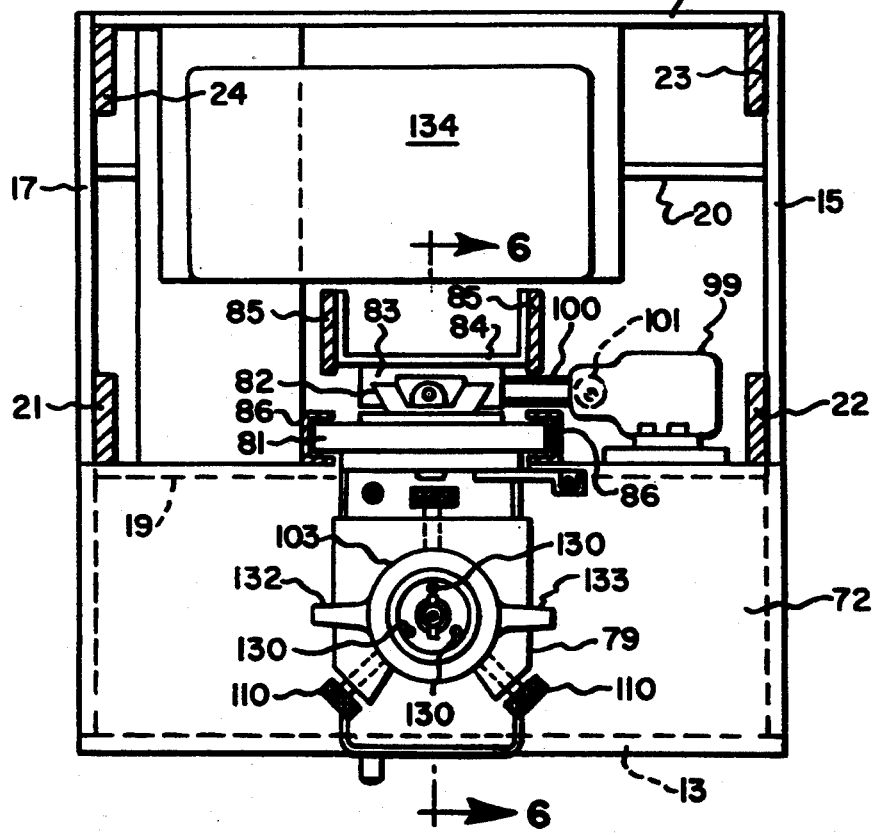
FIG. 5 is a cross sectional view taken substantially along line 5—5 of FIG. 1 and showing the shelf for supporting a liquid test vessel and the mounting structure therefor.

The convertible tensile test machine 10 includes a frame 11 consisting of a base 12 fabricated from flat ground metal bars 13, 14, 15 and 17 (FIG. 5) which are suitably fastened to each other by appropriate fasteners, not numbered, and are in the shape of a quadrangle. A strut 19 extends between and is suitably fastened to frame members 15 and 17. Another strut 20 (FIGS. 4 and 5) extends between and is suitably fastened to sides 15 and 17 and is parallel to strut 19. Columns 21, 22, 23 and 24, which are fabricated of hardened steel and have flat ground and parallel surfaces, are suitably attached by bolts to base 12 (FIGS. 1, 2, 3 and 5) and extend upwardly therefrom. Side member 25 (FIG. 1) has its ends suitably affixed at the tops of columns 21 and 22, and a parallel side member 27 (FIG. 3) has its opposite ends suitably affixed to the tops of columns 23 and 24. Side member 29 has its opposite ends suitably affixed to columns 21 and 22 substantially at the central portions thereof, and a parallel side member 30 has its opposite ends suitably affixed to columns 23 and 24 and lies parallel to side member 29. All of the foregoing members are fabricated of hardened steel and have flat ground and parallel surfaces.

A middle support plate 31 (FIGS. 1, 3 and 4) is mounted on a central portion of frame 11 which is located between the upper and lower portions thereof. Plate 31 has its central portion mounted in slot 32 of frame member 29 and its end 33 suitably affixed to frame member 30. Its forward end portion 34 extends in cantilevered fashion outwardly of frame member 29. A top support plate 35 (FIGS. 1 and 3) has its central portion extending through a slot 37 in cross member 25 and has its rear end 37 (FIG. 3) suitably affixed to the upper ends of struts 39 which have their lower ends suitably affixed to middle support plate 31.

Figure 4A:
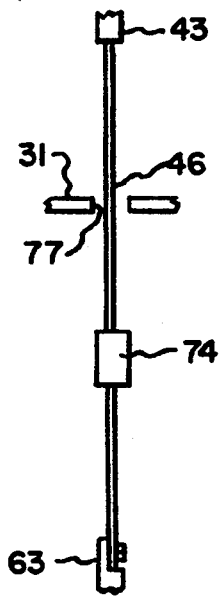
FIG. 4a is a fragmentary side elevational schematic view showing a test specimen on the machine being tested in the open environment.

Middle support plate 31 and top plate 37 support structure for driving carriage 40 along the upper portion of frame 11. Carriage 40 carries a load cell transducer unit 41 (FIG. 3) which has secured thereto a shaft 42 for carrying an attachment member or grip 43 which is to be attached to a specimen through a member 46 (FIG. 4a) during open environment testing or is attached to a rod 44 during testing in solution. More specifically, carriage 40 is mounted for vertical movement on the upper portion of frame 11 in the following manner. Hardened and precision ground shafts 45 have their lower ends secured in blind holes in middle support plate 31 and their upper ends pass through upper plate 35 and are secured by flange unit 47. Bearings 49 (FIG. 4) in carriage 40 guide carriage 40 for reciprocating movement along shafts 45. Carriage 40 is driven in such reciprocatory movement by a ball screw 50 which is suitably mounted in bearing units 51 and 52 (FIG. 3) suitably affixed on plates 31 and 35, respectively. Ball screw 50 is connected to carriage 40 by means of a flange unit 53. Ball screw 50 is driven by a DC servomotor 54 attached to a low backlash gear head 55 through a zero backlash flexible coupling 57. Motor 54 is mounted on plate 59 which is suitably mounted on plates 60 which are secured to top plate 37. An optical encoder 61 is mounted on a bracket 62 and is coupled to the lower end of ball screw 50 and is used to form a closed loop servo system by providing digital output proportional to the ball screw and motor rotation to a conventional electronic motor controller (not shown), typically being run by a personal computer (not shown). Bellows 66 and 68 (FIG. 3) surround the upper and lower portions, respectively, of shafts 45 to maintain them free of foreign matter. Bellows 66 is connected between plate 35 and the upper surface of carriage 40, and bellows 68 is connected between plate 31 and the lower surface of carriage 40.

A lower grip or attachment member 63 (FIGS. 2, 2a and 2b) is secured to the lower portion of frame 11. More specifically attachment member 63 is secured to pedestal 64 by a pin 65, member 63 being received in bore 67 of pedestal member 64 which has a broad base 69 which is secured to steel plate 70 by a plurality of screws 71. Plate 70 is suitably secured across portions of frame members 15 and 17 and across entire frame members 13 and 19. A plastic cover plate 72 is suitably secured to plate 70 and possesses a circular opening 73 which receives the base 69 of pedestal member 64. Pin 65 is selectively movable from pedestal member 64 so that different grips or attachment members 63 may be secured to the pedestal member.

When tensile test machine 10 is utilized for open environment testing, a test specimen, which is schematically depicted by numeral 74 (FIG. 4a), is attached between attachment members or grips 43 and 63, and carriage 40 is driven by ball screw 50 and the force applied thereto is measured by suitable measuring equipment (not shown) which receives its input from load cell transducer 41. At this point it is to be especially noted that the axes of grips 43 and 63 are in alignment and that the member 46 which secures the test specimen 74 to grip member 43 passes through slot 77 (FIG. 4a) of middle plate 31, considering that the test specimen is located below middle plate 31. At this time the tensile test machine 10 is configured as shown in FIG. 2 wherein there is no attachment thereon for the purpose of providing testing of a specimen in solution.

In accordance with the present invention, when it is desired to effect tensile testing in solution, the machine 10 is configured by attaching a shelf unit 79 and a lower grip attachment assembly 80 to the machine (FIGS. 1, 6 and 8). Pedestal 64 may remain attached to plate 70 when the machine is reconfigured for testing in solution, provided that it does not interfere with the structure used for the latter purpose. However, pedestal 64 may be disconnected if it interferes with the positioning of shelf unit 79. More specifically, the shelf unit 79 is attached to slide member 81 which has a dovetail connection at 82 with plate 83 which is suitably secured to channel member 84 mounted on struts 85 which have their upper ends affixed by suitable connectors to middle plate 31 and their lower ends by suitable brackets (not shown) to cross member 19 of frame 12. Member 81 rides in channels 86 which have their upper ends attached to cross frame member 29 and their lower ends attached to cross frame member 19.

The shelf 79 is selectively attached to plate 81 by means of a single screw 89. In this respect, a plate 90 is rigidly affixed to box member 91 of shelf 79, and it is selectively fitted between flange lips 92 (FIG. 6) of plate 81. Thereafter, a single screw 89 is passed through bore 93 in plate 90 and is received in tapped hole 94 of plate 81. Dovetail member 82 includes a nut member 95 thereon which receives threaded shaft 97 which is driven by motor 99 suitably secured to base 12 and connected to screw member 97 by means of a belt drive 100 which passes around motor pulley 101 and pulley 102 secured to the lower end of threaded member 97. In this manner detachable shelf 79 can be selectively attached to slide member 81 which is driven in a vertical direction by motor 99 in order to adjust the vertical level of the shelf for the purpose of receiving liquid containers of various sizes, depending on the size of the specimen which is to be tested therein.

A double walled vessel 103 is mountable on shelf 79. The lower end of vessel 103 is received in arcuate depression 104 of block 105 which is removably attached to shelf 79 by spring-biased detents 107 (FIGS. 3 and 8) located between the sides (not numbered) of shelf 79 and flanges 109 of member 105. A plurality of thumb screws 110 are threaded into member 105 for bearing against the bottom of vessel 103 to securely hold it in position on shelf 79.

A magnetic stirrer construction is provided for stirring liquid in vessel 103. In this respect, a magnetic stirring member 111 is housed in shelf 79 and an electrical lead 112 is connected thereto, with a plug 113 at the end of lead 112 which can pass through bore 114 in plate 90 and be received in receptacle 115 in plate 81 which is coupled to lead 117 which supplies current to activate magnetic stirrer 111, which when activated causes magnet member 119 to rotate within vessel 103 and thus stir liquid therein.

Further in accordance with the present invention, the specimen to be tested in solution is mounted on a lower grip attachment assembly 80, the lower end 120 of which is inserted into vessel 103. The attachment assembly 80 is selectively attachable to middle plate 31 by plate 121 (FIGS. 8 and 9) which is secured to plate 31 by a plurality of screws 122. Plate 121 has a slot 123 therein which is in alignment with slot 77 of middle plate 31 (FIG. 9). The aligned slots 77 and 123 permit rod 44 to pass therethrough. The upper end of rod 44 is secured to grip member 43, which is attached to the load cell transducer 41, and the lower end of rod 44 carries a grip member 124 to which is secured the upper end of test specimen 125, the lower end of which is connected to grip member 127 secured to plate 129 which is supported by three rods 130, the upper ends of which are affixed to plate 121. By this arrangement the test specimen 125 can be immersed in liquid in vessel 103, and its lower end can be rigidly secured to plate 129 while its upper end is being pulled when carriage 40 is moved upwardly by activation of ball screw 50. The tensile forces applied to specimen 125 can be measured by suitable measuring equipment associated with load cell transducer 41.

Suitable structure is used for providing liquid at a controlled temperature to vessel 103. In this respect, vessel 103 is double-walled glass, and it includes a space 131 between its walls. An entry nipple 133 receives liquid and an exit nipple 132 exhausts liquid. The liquid is provided by a suitable liquid control unit 134 which maintains liquid, preferably silicone liquid, at a controlled temperature and pumps it to vessel 103. Suitable conduits (not shown) convey the liquid to and from vessel 103.

Summarizing, it can thus be seen that testing of a specimen in liquid can be effected when shelf 79 and assembly 80 are mounted on the machine in the above-described manner. Furthermore, when shelf 79 is removed by the mere detachment of screw 89 and the unplugging of the electrical connection thereto and when assembly 80 is removed by detaching plate 121 from middle support plate 31, testing in the open environment can be effected by effectively securing a test specimen between grip members 43 and 63. In order to effectuate the dual capability of the tensile test machine 10, cantilevered portion 34 of middle plate 31 and plate 121 must have slots 77 and 123, respectively, therein to permit connection of the test specimen by a connector, such as 44, to upper grip 43. It will be appreciated, however, that the openings in the plate portion 34 and in plate 121 need not be in the nature of slots as shown but may be of any other suitable configuration.

Panels 140 and 141 are suitably attached to the front of the machine for carrying various control knobs and the like.

It can thus be seen that the dual capability tensile testing machine 10 of the present invention is manifestly capable of achieving the above-enumerated objects, and while preferred embodiments of the present invention have been disclosed, it will be appreciated that it is not limited thereto but may be otherwise embodied within the scope of the following claims.

What is claimed is:

1. A convertible tensile test machine having a dual capability for selectively testing specimens in an open environment or in solution comprising a frame having an upper portion and a lower portion and a central portion therebetween, a support plate on said central portion of said frame, a carriage on said upper portion of said frame, a load cell transducer on said carriage, means for driving said carriage toward and away from said support plate, an upper grip coupled to said load cell transducer, a lower grip coupled to said lower portion of said frame, a first opening in said support plate, a connector member for attachment to said upper grip and for passage through said first opening for connection to a specimen located between said support plate and said lower portion of said frame when said specimen is connected to said lower grip, a shelf for supporting a vessel for containing a solution, means for selectively mounting said shelf on said lower portion of said frame, an attachment assembly for carrying a second lower grip for attachment to a specimen which is to be tested in said vessel mounted on said shelf, an attachment plate on said attachment assembly for selective attachment to said support plate for supporting said attachment assembly thereon, and a second opening in said attachment plate for alignment with said first opening in said support plate for permitting passage therethrough of said connector member which also passes through said first opening in said support plate.

2. A convertible tensile test machine for selectively testing a first specimen having upper and lower portions in an open environment or testing a second specimen having upper and lower portions in solution comprising a frame having a lower portion and an upper portion and a central portion therebetween, first attachment means on said lower portion of said frame for attachment to said lower portion of said first specimen for testing in the open environment, a load cell carriage, load cell carriage mounting means for mounting said load cell carriage on said upper portion of said frame for movement toward and away from said lower portion of said frame, a load cell on said load cell carriage, second attachment means coupled to said load cell for attachment to said upper portion of said first specimen for testing in the open environment or for attachment to said upper portion of said second specimen for testing in solution, rod means for attachment between said second attachment means and said upper portion of said first specimen, a support plate mounted on said central portion of said frame, a portion on said support plate projecting between said first and second attachment means, first opening means in said support plate for permitting said rod means to pass through said support plate, a shelf for supporting a vessel containing solution, shelf attaching means for selectively attaching said shelf on said lower portion of said frame below said support plate, third attachment means for attachment to said lower portion of said second specimen for testing in solution, connecting means for connecting said third attachment means to said support plate and for spacing said third attachment means from said support plate so as to permit said third attachment means to be located in said vessel supported on said shelf, and second opening means in said connecting means in alignment with said first opening means for permitting said rod means to pass therethrough when said lower portion of said second specimen is connected to said support plate by said connecting means, whereby said first specimen can be tested in an open environment when said shelf is not positioned on said lower portion of said frame and when said third attachment means is not connected to said support plate, and said second specimen can be tested in solution when said shelf is positioned on said lower portion of said frame and said third attachment means is connected to said support plate.

3. A convertible tensile test machine as set forth in claim 2 wherein said shelf attaching means for attaching said shelf to said frame includes shelf adjusting means for selectively positioning said shelf at various locations on said lower portion of said frame.

4. A convertible tensile test machine as set forth in claim 3 wherein said shelf adjusting means comprises a motor, guide means for supporting said shelf attaching means, and a screw drive operatively coupled between said motor and said shelf attaching means to drive said shelf attaching means along said guide means.

5. A convertible tensile test machine as set forth in claim 2 wherein said means for mounting said carriage for movement toward and away from said lower portion of said frame comprises guide means located above said support plate on said upper portion of said frame, a screw drive coupled to said carriage, and motor means for driving said screw drive.

6. A convertible tensile test machine as set forth in claim 5 wherein said shelf attaching means for attaching said shelf to said frame includes shelf adjusting means for selectively positioning said shelf at various locations on said lower portion of said frame.

7. A convertible tensile test machine as set forth in claim 6 wherein said shelf adjusting means comprises a motor, guide means for supporting said shelf attaching means, and a screw drive operatively coupled between said motor and said shelf attaching means to drive said shelf attaching means along said guide means.

8. A convertible tensile test machine having a dual capability for selectively testing a first specimen having upper and lower portions in the open environment or for testing a second specimen having upper and lower portions in solution comprising a frame, an upper grip assembly on said frame carrying an upper grip for gripping said upper portion of said first specimen, a lower grip assembly carrying a first lower grip aligned with said upper grip on said frame for gripping said lower portion of said first specimen during open environment testing, a shelf selectively mountable between said upper and lower grips for supporting a vessel which is to contain solution, and a second lower grip assembly selectively mountable on said frame for carrying a second lower grip for alignment with said upper grip which grips said upper portion of said second specimen and for attachment to said lower portion of said second specimen which is to be immersed in said solution in said vessel supported on said shelf.

9. A convertible tensile test machine as set forth in claim 8 including a load cell transducer coupled to said upper grip assembly.

* * * * *